US006713046B1

(12) United States Patent
Meade

(10) Patent No.: US 6,713,046 B1
(45) Date of Patent: *Mar. 30, 2004

(54) MAGNETIC RESONANCE IMAGING AGENTS FOR THE DELIVERY OF THERAPEUTIC AGENTS

(75) Inventor: Thomas J. Meade, Altadena, CA (US)

(73) Assignee: Research Corporation Technologies, Tucson, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/179,927

(22) Filed: Oct. 27, 1998

Related U.S. Application Data

(60) Provisional application No. 60/063,328, filed on Oct. 27, 1997.

(51) Int. Cl.$^7$ ............................................. A61B 5/055
(52) U.S. Cl. ................. 424/9.363; 424/9.34; 424/9.341
(58) Field of Search ........................... 424/9.34, 9.341, 424/9.363, 9.36, 9.361

(56) References Cited

U.S. PATENT DOCUMENTS

| | | | |
|---|---|---|---|
| 4,637,988 A | | 1/1987 | Hinshaw et al. |
| 4,647,447 A | * | 3/1987 | Gries et al. ................. 424/9.36 |
| 4,678,667 A | * | 7/1987 | Meares et al. ............. 424/1.53 |
| 4,822,594 A | | 4/1989 | Gibby |
| 4,837,169 A | | 6/1989 | Toner |
| 4,877,872 A | | 10/1989 | Morgan et al. |
| 4,885,363 A | * | 12/1989 | Tweedle et al. ............. 540/465 |
| 5,087,440 A | | 2/1992 | Cacheris et al. |
| 5,095,099 A | | 3/1992 | Parkinson et al. |
| 5,133,956 A | | 7/1992 | Garlich et al. |
| 5,155,215 A | | 10/1992 | Ranney |
| 5,188,816 A | | 2/1993 | Sherry et al. |
| 5,219,553 A | | 6/1993 | Kraft et al. |
| 5,230,883 A | | 7/1993 | Kornguth et al. |
| 5,256,395 A | * | 10/1993 | Barbet et al. ............... 424/1.57 |
| 5,262,532 A | | 11/1993 | Tweedle et al. |
| 5,292,414 A | | 3/1994 | Sessler et al. |
| 5,310,539 A | | 5/1994 | Williams |
| 5,322,681 A | | 6/1994 | Klaveness |
| 5,332,567 A | * | 7/1994 | Goldenberg ............... 424/1.49 |
| 5,338,532 A | | 8/1994 | Tomalia et al. |
| 5,358,704 A | | 10/1994 | Desreux et al. |
| 5,407,657 A | | 4/1995 | Unger et al. |
| 5,419,893 A | | 5/1995 | Berg et al. |
| 5,428,154 A | * | 6/1995 | Gansow et al. ............. 540/465 |
| 5,428,156 A | * | 6/1995 | Mease et al. ................ 540/474 |
| 5,446,145 A | | 8/1995 | Love et al. |
| 5,466,438 A | | 11/1995 | Unger et al. |
| 5,466,439 A | | 11/1995 | Gibby et al. |
| 5,531,978 A | | 7/1996 | Berg et al. |
| 5,554,748 A | | 9/1996 | Sieving et al. |
| 5,622,821 A | | 4/1997 | Selvin et al. |
| 5,707,605 A | | 1/1998 | Meade et al. |
| 5,914,095 A | | 6/1999 | Watson |
| 5,955,605 A | * | 9/1999 | Axworthy et al. .......... 540/474 |
| 5,980,862 A | | 11/1999 | Meade et al. |

FOREIGN PATENT DOCUMENTS

| | | |
|---|---|---|
| CA | 2139374 | 7/1995 |
| CA | 2182686 | 8/1995 |
| CA | 2197074 | 2/1996 |
| WO | WO 90/12050 | 10/1990 |
| WO | WO 92/19264 | 11/1992 |
| WO | WO 95/27705 | 10/1995 |
| WO | WO 95/28966 | 11/1995 |
| WO | WO 95/31444 | 11/1995 |
| WO | 95/32741 | 12/1995 |
| WO | 96/23526 | 8/1996 |
| WO | 96/38184 | 12/1996 |
| WO | 97/21431 | 6/1997 |
| WO | WO 97/32862 | 9/1997 |
| WO | 97/36619 | 10/1997 |
| WO | WO 99/21592 | 5/1999 |

OTHER PUBLICATIONS

Moats, et al., "A 'Smart' Magnetic Resonance Imaging Agent That Reports on Specific Enzymatic Activity," Angew. Chem. Int. Ed. Engl., 36(7): 726–728 (Apr. 1997).
Agauyo, J.B., et al. "Nuclear Magnetic Resonance Imaging of a Single Cell," Nature, Letters to Nature 322:190–191 (Jul. 10, 1986).
Alexander, "Design and Synthesis of Macrocyclic Ligands and Their Complexes of Lanthanides and Antinides," Chem. Review, 95:273–342 (1995).
Borch, R.F., et al. "The Cyanohydridoborate Anion as a Selective Reducing Agent," Journal of the American Chemical Society 93 (12): 2897–2904 (Jun. 16, 1971).
Cho, Z.H., et al. "Some Experiences on a 4 $\mu\mu$m NMR Microscopy," Book of Abstracts, vol. 1, p.233, Society of Magnetic Resonance in Medicine, 6th Annual Meeting and Exhibition, Aug. 17–21, 1987, New York City, NY.
Grynkiewicz, G., et al. "A New Generation of Ca2+ Indicators with Greatly Improved Fluorescence Properties," The Journal of Biological Chemistry, 260(6): 3440–3450 (1985).
Hennessy, M.J., et al. "NMR Surface Coil Microscopy," Book of Abstracts, vol. 2, p.461–462, Society of Magnetic Resonance in Medicine, 5th Annual Meeting and Exhibition, Aug. 19–22, 1986, Montreal, Quebec, Canada.
Hoult, D.I., et al. "The Signal–to–Noise Ratio of the Nuclear Magnetic Resonance Experiment," Journal of Magnetic Resonance, 24: 71–85 (1976).
Jackels, "Section III: Enhancement Agents for Magnetic Resonance and Ultrasound Imaging: Chapter 20: Enhancement Agents for Magnetic Resonance Imaging: Fundamentals," Pharm. Med. Imag. Section III, Chap. 20, pp. 645–661 (1990).

(List continued on next page.)

Primary Examiner—Michael G. Hartley
(74) Attorney, Agent, or Firm—Robin M. Silva; Renee M. Kosslak; Dorsey & Whitney LLP

(57) ABSTRACT

The invention relates to novel magnetic resonance imaging contrast agents and methods of delivering therapeutically active agents.

16 Claims, 2 Drawing Sheets

OTHER PUBLICATIONS

Jacobs and Fraser, "Magnetic Resonance Microscopy of Embryonic Cell Lineages and Movements," *Science*, 263:681–684 (1994).

Johnson, G.A., et al., "MR Microscopy at 7.0 T," Works in Progress, Society of Magnetic Resonance in Medicine, Sixth Annual Meeting and Exhibition, Aug. 17–21, 1987, New York City, NY. p.23.

Li, et al., "A Calcium–Sensitive Magnetic Resonance Imaging Contrast Agent," J. Am. Chem. Soc., 121:1413–1414 (1999).

Meade, T.J. et al., "Hydrophobic, Regiospecific Guest Binding by Transition–Metal Host Complexes Having Permanent Voids as Revealed by FT–NMR Relaxation Studies," J. Am. Chem. Soc., 108:1954–1962 (1986).

Meyer et al., "Advances in Macrocyclic Gadolinium Complexes as Magnetic Resonance Imaging Contrast Agents," Investigative Radiology, 25(1):S53–S55 (Sep. 1990).

Moi, M.K., et al. "The Peptide Way to Macrocyclic Bifunctional Chelating Agents: Synthesis of 2–(p–Nitrobenzyl) 1,4,7,10–tetraazacyclododecan–N, N", N"", N""""–tetraacetic Acid and Study of Its Yttrium (III) Complex," J. Am. Chem. Soc. 110(18):6266–6267 (1988).

Nijhof, E.J., et al. "High–Resolution Proton Imaging at 4.7 Tesla," Proceedings of Soc. Magn. Reson. Med., P.925 (1987).

Runge, V.M., et al. "Future Directions in Magnetic Resonance Contrast Media," Top Magn. Reson. Imaging., 3(2):85–97 (1991).

Russell, E.J., et al. "Multicenter Double–Blind PlaceboControlled Study of Gadopentetate Dimeglumine as an MR Contrast Agent: Evaluation in Patients with Cerebral Lesions," American Journal of Roentgenology, 152:813–823 (Apr. 1989).

Shukla, et al., "Design of Conformationally Rigid Dimeric MRI Agents," Magnetic Resoance in Medicine, 36(6): 928–931 (1996).

Sillerud, L.O., et al. "Proton NMR Microscopy of Intact Multicellular Tumor Spheroids," Book of Abstracts, vol. 1, p.468, Society of Magnetic Resonance in Medicine, 6th Annual Meeting and Exhibition, Aug. 17–21, 1987, New York City, NY.

Staubli and Meade, "The Design and Synthesis of Fluorescently Detectable Magnetic Resonance imaging Agents for Embryonic Cell Lineage Analysis," *American Chemical Society: Division of Inorganic Chemistry*, 209th ACS National Meeting, Anaheim, California, Abstract No. 385 (Apr. 2–6, 1995).

Tsien, R.Y. "New Calcium Indicators and Buffers with High Selectivity Against Magnesium and Protons: Design, Synthesis, and Properties of Prototype Structures," Biochemistry, 19(11): 2396–2404 (1980).

Tweedle, M.F., et al. "Considerations Involving Paramagnetic Coordination Compounds as Useful NMR Contrast Agents," Nucl. Med. Bio. 15(1):31–36 (1988).

* cited by examiner

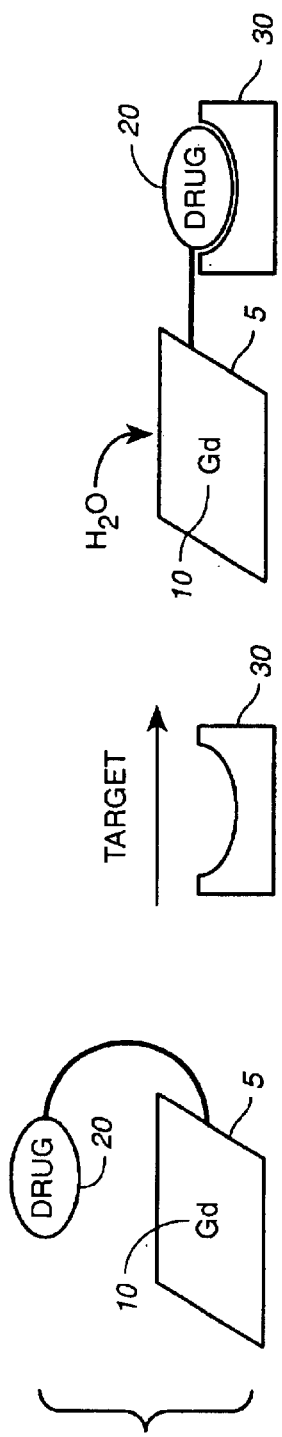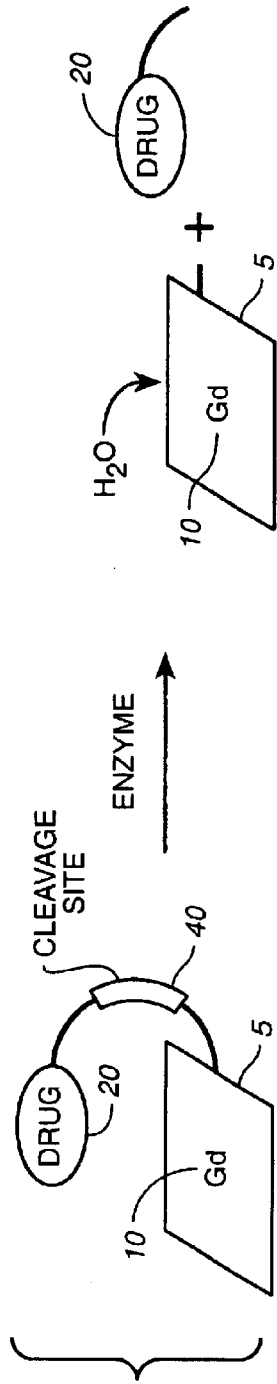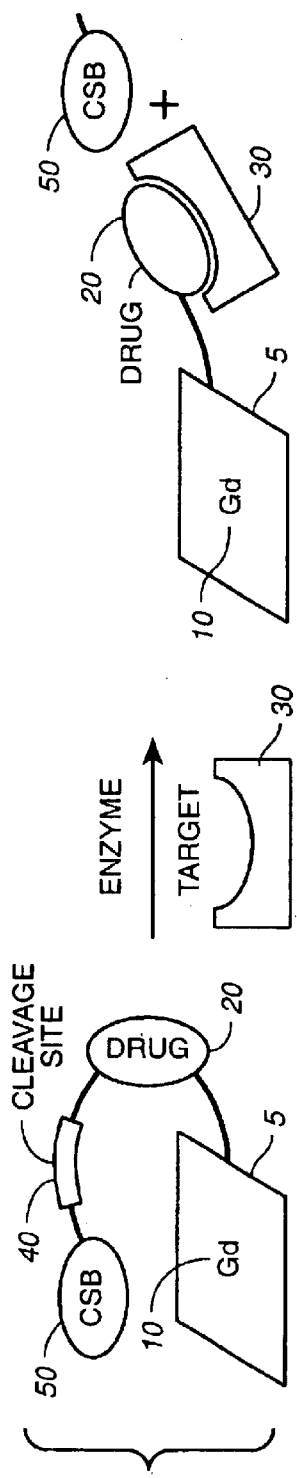

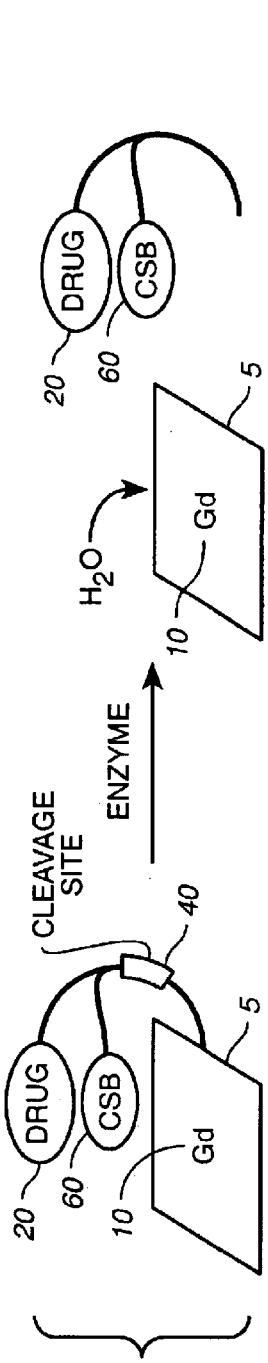
FIG._2A
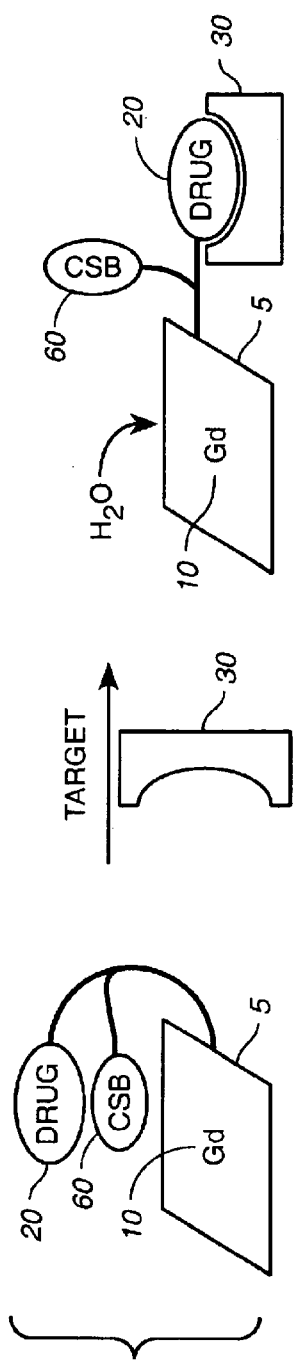
FIG._2B
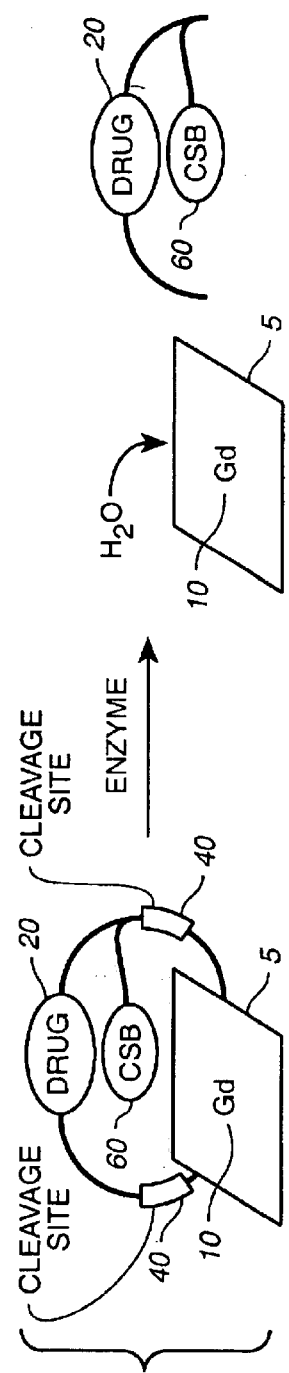
FIG._2C

MAGNETIC RESONANCE IMAGING AGENTS FOR THE DELIVERY OF THERAPEUTIC AGENTS

This application is a continuing application of U.S. Ser. No. 60/063,328 filed Oct. 27, 1997.

FIELD OF THE INVENTION

The invention relates to novel magnetic resonance imaging contrast agents and methods of delivering therapeutically active substances.

BACKGROUND OF THE INVENTION

Magnetic resonance imaging (MRI) is a diagnostic and research procedure that uses high magnetic fields and radio-frequency signals to produce images. The most abundant molecular species in biological tissues is water. It is the quantum mechanical "spin" of the water proton nuclei that ultimately gives rise to the signal in all imaging experiments. In MRI the sample to be imaged is placed in a strong static magnetic field (1–12 Tesla) and the spins are excited with a pulse of radio frequency (RF) radiation to produce a net magnetization in the sample. Various magnetic field gradients and other RF pulses then act on the spins to code spatial information into the recorded signals. MRI is able to generate structural information in three dimensions in relatively short time spans.

The Image

MR images are typically displayed on a gray scale with black the lowest and white the highest measured intensity (I). This measured intensity I=C * M, where C is the concentration of spins (in this case, water concentration) and M is a measure of the magnetization present at time of the measurement. Although variations in water concentration (C) can give rise to contrast in MR images, it is the strong dependence of the rate of change of M on local environment that is the source of image intensity variation in MRI. Two characteristic relaxation times, $T_1$ & $T_2$, govern the rate at which the magnetization can be accurately measured. $T_1$ is the exponential time constant for the spins to decay back to equilibrium after being perturbed by the RF pulse. In order to increase the signal-to-noise ratio (SNR) a typical MR imaging scan (RF & gradient pulse sequence and data acquisition) is repeated at a constant rate for a predetermined number of times and the data averaged. The signal amplitude recorded for any given scan is proportional to the number of spins that have decayed back to equilibrium since the previous scan. Thus, regions with rapidly decaying spins (i.e. short $T_1$ values) will recover all of their signal amplitude between successive scans.

The measured intensities in the final image will accurately reflect the spin density (i.e. water content). Regions with long $T_1$ values compared to the time between scans will progressively lose signal until a steady state condition is reached and will appear as darker regions in the final image. Changes in $T_2$ (spin-spin relaxation time) result in changes in the signal linewidth (shorter $T_2$ values) yielding larger linewidths. In extreme situations the linewidth can be so large that the signal is indistinguishable from background noise. In clinical imaging, water relaxation characteristics vary from tissue to tissue, providing the contrast which allows the discrimination of tissue types. Moreover, the MRI experiment can be setup so that regions of the sample with short $T_1$ values and/or long $T_2$ values are preferentially enhanced so called $T_1$-weighted and $T_2$-weighted imaging protocol.

MRI Contrast Agents

There is a rapidly growing body of literature demonstrating the clinical effectiveness of paramagnetic contrast agents (currently 8 are in clinical trials or in use). The capacity to differentiate regions/tissues that may be magnetically similar but histologically distinct is a major impetus for the preparation of these agents [1, 2]. In the design of MRI agents, strict attention must be given to a variety of properties that will ultimately effect the physiological outcome apart from the ability to provide contrast enhancement [3]. Two fundamental properties that must be considered are biocompatability and proton relaxation enhancement. Biocompatability is influenced by several factors including toxicity, stability (thermodynamic and kinetic), pharmacokinetics and biodistribution. Proton relaxation enhancement (or relaxivity) is chiefly governed by the choice of metal and rotational correlation times.

The first feature to be considered during the design stage is the selection of the metal atom, which will dominate the measured relaxivity of the complex. Paramagnetic metal ions, as a result of their unpaired electrons, act as potent relaxation enhancement agents. They decrease the $T_1$ and $T_2$ relaxation times of nearby ($r^6$ dependence) spins. Some paramagnetic ions decrease the $T_1$ without causing substantial linebroadening (e.g. gadolinium (III), ($Gd^{3+}$)), while others induce drastic linebroadening (e.g. superparamagnetic iron oxide). The mechanism of $T_1$ relaxation is generally a through space dipole-dipole interaction between the unpaired electrons of the paramagnet (the metal atom with an unpaired electron) and bulk water molecules (water molecules that are not "bound" to the metal atom) that are in fast exchange with water molecules in the metal's inner coordination sphere (are bound to the metal atom).

For example, regions associated with a $Gd^{3+}$ ion (near-by water molecules) appear bright in an MR image where the normal aqueous solution appears as dark background if the time between successive scans if the experiment is short (i.e. $T_1$ weighted image). Localized $T_2$ shortening caused by superparamagnetic particles is believed to be due to the local magnetic field inhomogeneities associated with the large magnetic moments of these particles. Regions associated with a superparamagnetic iron oxide particle appear dark in an MR image where the normal aqueous solution appears as high intensity background if the echo time (TE) in the spin-echo pulse sequence experiment is long (i.e. $T_2$-weighted image). The lanthanide atom $Gd^{3+}$ is by the far the most frequently chosen metal atom for MRI contrast agents because it has a very high magnetic moment ($u^2$=63BM$^2$), and a symmetric electronic ground state, ($S^8$). Transition metals such as high spin Mn(II) and Fe(III) are also candidates due to their high magnetic moments.

Once the appropriate metal has been selected, a suitable ligand or chelate must be found to render the complex nontoxic. The term chelator is derived from the Greek word chele which means a "crabs claw", an appropriate description for a material that uses its many "arms" to grab and hold on to a metal atom (see DTPA below). Several factors influence the stability of chelate complexes include enthalpy and entropy effects (e.g. number, charge and basicity of coordinating groups, ligand field and conformational effects). Various molecular design features of the ligand can be directly correlated with physiological results. For example, the presence of a single methyl group on a given ligand structure can have a pronounced effect on clearance rate. While the addition of a bromine group can force a given complex from a purely extracellular role to an effective agent that collects in hepatocytes.

Diethylenetriaminepentaacetic (DTPA) chelates and thus acts to detoxify lanthanide ions. The stability constant (K) for Gd(DTPA)$^{2-}$ is very high (logK=22.4) and is more commonly known as the formation constant (the higher the logK, the more stable the complex). This thermodynamic parameter indicates the fraction of Gd$^{3+}$ ions that are in the unbound state will be quite small and should not be confused with the rate (kinetic stability) at which the loss of metal occurs ($k_p/k_d$). The water soluble Gd(DTPA)$^{2-}$ chelate is stable, nontoxic, and one of the most widely used contrast enhancement agents in experimental and clinical imaging research. It was approved for clinical use in adult patients in June of 1988. It is an extracellular agent that accumulates in tissue by perfusion dominated processes.

To date, a number of chelators have been used, including diethylenetriaminepentaacetic (DTPA), 1,4,7,10-tetraazacyclododecane'-N,N'N",N'''-tetracetic acid (DOTA), and derivatives thereof. See U.S. Pat. Nos. 5,155,215, 5,087, 440, 5,219,553, 5,188,816, 4,885,363, 5,358,704, 5,262,532, and Meyer et al., Invest. Radiol. 25: S53 (1990).

Image enhancement improvements using Gd(DTPA) are well documented in a number of applications (Runge et al., Magn, Reson. Imag. 3:85 (1991); Russell et al., AJR 152:813 (1989); Meyer et al., Invest. Radiol. 25:S53 (1990)) including visualizing blood-brain barrier disruptions caused by space occupying lesions and detection of abnormal vascularity. It has recently been applied to the functional mapping of the human visual cortex by defining regional cerebral hemodynamics (Belliveau et al., (1991) 254:719).

Another chelator used in Gd contrast agents is the macrocyclic ligand 1,4,7,10-tetraazacyclododecane-N,N',N"N'''-tetracetic acid (DOTA). The Gd-DOTA complex has been thoroughly studied in laboratory tests involving animals and humans. The complex is conformationally rigid, has an extremely high formation constant (logK=28.5), and at physiological pH possess very slow dissociation kinetics. Recently, the GdDOTA complex was approved as an MRI contrast agent for use in adults and infants in France and has been administered to over 4500 patients.

Previous work has resulted in MRI contrast agents that report on physiologic or metabolic processes within a biological or other type of sample. As described in U.S. Pat. No. 5,707,605, PCT US96/08549, and U.S. Ser. No. 09/134,072, MRI contrast agents have been constructed that allow an increase in contrast as a result of the interaction of a blocking moiety present on the agent with a target substance. That is, in the presence of the target substance, the exchange of water in one or more inner sphere coordination sites of the contrast agent is increased, leading to a brighter signal; in the absence of the target substance, the exchange of water is hindered and the image remains dark. Thus, the previous work enables imaging of physiological events rather than just structure.

However, it would be a further improvement to be able to deliver therapeutic agents and follow their delivery via MRI. Accordingly, it is an object of the present invention to provide MRI contrast or enhancement agents which allow the visualization and detection of the delivery of therapeutic agents within an animal, tissue or cells.

SUMMARY OF THE INVENTION

In accordance with the above objects, the invention provides MRI agents comprising a chelator and a paramagnetic metal ion that is coordinatively saturated by the chelator and a therapeutic blocking moiety, wherein said therapeutic blocking moiety is covalently attached to said chelator such that the rapid exchange of water in at least one coordination site is hindered, wherein said therapeutic blocking moiety comprises at least a therapeutically active agent, wherein the exchange of water in at least one coordination site is increased upon delivery of said therapeutically active agent to its physiological target resulting in a therapeutic effect.

In an additional aspect, the invention provides MRI agents having the formula:

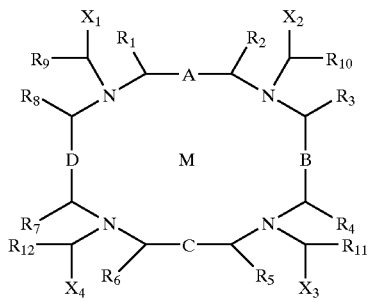

wherein
  M is a paramagnetic metal ion selected from the group consisting of Gd(III), Fe(III), Mn(II), Yt(III), Cr(III) and Dy(III);
  A, B, C and D are either single bonds or double bonds;
  $X_1$, $X_2$, $X_3$ and $X_4$ are —OH, —COO—, —CH$_2$OH—CH$_2$COO—, a substitution group, a therapeutic blocking moiety or a targeting moiety;
  $R_1$–$R_{12}$ are hydrogen, a substitution group, a therapeutic blocking moiety or a targeting moiety; wherein at least one of $X_1$–$X_4$ and $R_1$–$R_{12}$ is a therapeutic blocking moiety.

In a further aspect, the MRI agents have the formula:

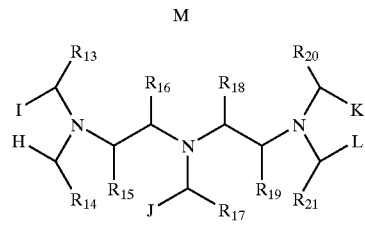

wherein
  M is a paramagnetic metal ion selected from the group consisting of Gd(III), Fe(III), Mn(II), Yt(III), Cr(III) and Dy(III);
  H, I, J, K and L are —OH, —COO—, —CH$_2$OH—CH$_2$COO—, a substitution group, a therapeutic blocking moiety or a targeting moiety;
  $R_{13}$–$R_{21}$ are hydrogen, a substitution group, a therapeutic blocking moiety or a targeting moiety; wherein at least one of H, I, J, K and L nd $R_{13}$–$R_{21}$ is a therapeutic blocking moiety.

In an additional aspect, the invention provides methods of treating a disorder associated with a therapeutically active agent comprising administering an MRI agent of the invention to produce a magnetic resonance image of said cell, tissue or patient.

In a further aspect, the invention provides methods of magnetic resonance imaging of a cell, tissue or patient comprising administering an MRI agent to a cell, tissue or patient and rendering a magnetic resonance image of said cell, tissue or patient.

BRIEF DESCRIPTION OF THE DRAWINGS

FIGS. 1A, 1B and 1C depict some embodiments of the invention. FIG. 1A depicts the situation wherein the drug 20 provides the coordination atom to the metal ion 10 (shown as Gd, herein) in the chelate 5, although the coordination atom may be contributed by a linker, a coordination site barrier, or a cleavage site (FIG. 1B). Upon exposure to the physiological target 30, a conformational change occurs, allowing the rapid exchange of water. FIG. 1B is similar, except a cleavage site 40 is used, which upon exposure to a cleavage agent cleaves off the drug 20. FIG. 1C depicts the use of a coordination site barrier 50, which in the absence of a cleavage agent such as an enzyme hinders the exchange of water. However, after cleavage, the target 30 is able to interact with the drug 20. Although not depicted, a targeting moiety may also be included in any of the embodiments herein; for example, a targeting moiety used to target the drug may attached to the drug 20 in FIG. 1A, either between the metal chelate and the drug or as a "terminal group" to the drug. Alternatively, the targeting moiety may be attached to the chelate 5 in another position. Similarly, a targeting moiety may be attached to the FIGS. 1B and 1C embodiments between the cleavage site 40 and the drug 20, or as a terminal group.

FIGS. 2A, 2B and 2C depict the use of coordination site barriers 60. A variety of conformations may be utilized as generally described for FIG. 1, including the use of targeting groups. It should also be noted that additional cleavage sites may be put into the system, for example to cleave the coordination site barrier 60 from the drug 20 in FIG. 2C.

DETAILED DESCRIPTION OF THE INVENTION

The present invention provides magnetic resonance imaging (MRI) contrast agents which can detect the delivery of therapeutically active agents as a result of an interaction of a physiological target agent and the MRI agents of the invention. The MRI agents of the invention are relatively inactive, or have weak relaxivity, as contrast enhancement agents in the absence of the physiological target substance, and are activated, thus altering the MR image, upon the delivery of the therapeutically active agent.

The imaging of the delivery of the therapeutically active agent can occur in two basic ways. In one embodiment, it is the actual interaction of the therapeutically active agent with its target that causes the MRI agent to turn "on", as described below; that is, as a result of the presence of the physiological target, the MRI agent undergoes a reorganization that can include the cleavage of the therapeutically active agent off the remainder of MRI agent, causing an increase in signal as a result of an increase in the exchange of water in an inner coordination site. Alternatively, it is the delivery event of the active agent that is imaged; that is, the therapeutically active agent is cleaved off of the MRI agent as a result of exposure to a cleavage agent such as a protease, freeing the therapeutically active agent to interact with its target. In general, it is the former that is discussed herein, although as will be appreciated by those in the art, either possibility can occur.

Viewed simplistically, this "trigger" mechanism, whereby the contrast agent is "turned on" (i.e. increases the relaxivity) by the delivery of the therapeutically active agent, is based on a dynamic equilibrium that affects the rate of exchange of water molecules in one or more coordination sites of a paramagnetic metal ion contained in the MRI contrast agents of the present invention. In turn, the rate of exchange of the water molecule is determined by the presence or absence of the therapeutic blocking moiety on the MRI agent. Thus, in the presence of the therapeutically active agent, the metal ion complexes of the invention which chelate the paramagnetic ion have reduced coordination sites available which can rapidly exchange with the water molecules of the local environment. In such a situation, the water coordination sites are substantially occupied or blocked by the coordination atoms of the chelator and at least one therapeutic blocking moiety. Thus, the paramagnetic ion has essentially no water molecules in its "inner-coordination sphere", i.e. actually bound to the metal when the target substance is absent. It is the interaction of the paramagnetic metal ion with the protons on the inner coordination sphere water molecules and the rapid exchange of such water molecules that cause the high observed relaxivity, and thus the imaging effect, of the paramagnetic metal ion. Accordingly, if all the coordination sites of the metal ion in the metal ion complex are occupied with moieties other than water molecules, as is the case when the therapeutic blocking moiety is present, there is little if any net enhancement of the imaging signal by the metal ion complexes of the invention. However, when the therapeutically active agent is removed (either as a result of an interaction with its physiological target or by cleavage), this effectively frees at least one of the inner-sphere coordination sites on the metal ion complex. The water molecules of the local environment are then available to reversibly occupy the inner-sphere coordination site or sites, which will cause an increase in the rate of exchange of water and relaxivity of the metal ion complex toward water thereby producing image enhancement which is a measure of the delivery of the therapeutically active agent.

Generally, a 2 to 5% change in the MRI signal used to generate the image is sufficient to be detectable. Thus, it is preferred that the agents of the invention display an increase the MRI signal by at least 2 to 5% upon delivery of the therapeutically active agent as compared to the signal when the therapeutically active agent is present on the MRI agent. Signal enhancement of 2 to 90% is preferred, and 10 to 50% is more preferred for each coordination site made available by the delivery of the therapeutically active agent. That is, when the therapeutic blocking moiety occupies two or more coordination sites, the release of the therapeutic blocking moiety can result in a significant increase in the signal or more as compared to a single coordination site.

It should be understood that even in the presence of the therapeutic blocking moiety, at any particular coordination site, there will be a dynamic equilibrium for one or more coordination sites as between a coordination atom of the therapeutic blocking moiety and water molecules. That is, even when a coordination atom is tightly bound to the metal, there will be some exchange of water molecules at the site. However, in most instances, this exchange of water molecules is neither rapid nor significant, and does not result in significant image enhancement. However, upon delivery of the therapeutically active agent, the therapeutic blocking moiety dislodges from the coordination site and the exchange of water is increased, i.e. rapid exchange and therefore an increase in relaxivity may occur, with significant image enhancement.

Accordingly, the MRI agents of the invention comprise a metal ion complex. The metal ion complexes of the invention comprise a paramagnetic metal ion bound to a complex comprising a chelator and a therapeutic blocking moiety. By "paramagnetic metal ion", "paramagnetic ion" or "metal ion" herein is meant a metal ion which is magnetized parallel or antiparallel to a magnetic field to an extent proportional to the field. Generally, these are metal ions which have unpaired electrons; this is a term understood in the art. Examples of suitable paramagnetic metal ions, include, but are not limited to, gadolinium III (Gd+3 or Gd(III)), iron III (Fe+3 or Fe(III)), manganese II (Mn+2 or Mn(II)), yttrium III (Yt+3 or Yt(III)), dysprosium (Dy+3 or Dy(III)), and chromium (Cr(III) or Cr+3). In a preferred embodiment the paramagnetic ion is the lanthanide atom Gd(III), due to its high magnetic moment ($u^2$=63BM2), a symmetric electronic ground state (S8), and its current approval for diagnostic use in humans.

In addition to the metal ion, the metal ion complexes of the invention comprise a chelator and a therapeutic blocking moiety which may be covalently attached to the chelator. Due to the relatively high toxicity of many of the paramagnetic ions, the ions are rendered nontoxic in physiological systems by binding to a suitable chelator. Thus, the substitution of therapeutic blocking moieties in coordination sites of the chelator, which upon delivery of the therapeutically active agent vacate the coordination sites in favor of water molecules, may render the metal ion complex more toxic by decreasing the half-life of dissociation for the metal ion complex. Thus, in a preferred embodiment, only a single coordination site is occupied or blocked by a therapeutic moeity. However, for some applications, e.g. use in experimental animals, tissue samples, etc., the toxicity of the metal ion complexes may not be of paramount importance. Similarly, some metal ion complexes are so stable that even the replacement of one or more additional coordination atoms with a therapeutic blocking moiety does not significantly effect the half-life of dissociation. For example, DOTA, described below, when complexed with Gd(III) is extremely stable. Accordingly, when DOTA serves as the chelator, several of the coordination atoms of the chelator may be replaced with therapeutic blocking moieties without a significant increase in toxicity. Additionally such an agent would potentially produce a larger signal since it has two or more coordination sites which are rapidly exchanging water with the bulk solvent.

There are a variety of factors which influence the choice and stability of the chelate metal ion complex, including enthalpy and entropy effects (e.g. number, charge and basicity of coordinating groups, ligand field and conformational effects).

In general, the chelator has a number of coordination sites containing coordination atoms which bind the metal ion. The number of coordination sites, and thus the structure of the chelator, depends on the metal ion. The chelators used in the metal ion complexes of the present invention preferably have at least one less coordination atom (n−1) than the metal ion is capable of binding (n), since at least one coordination site of the metal ion complex is occupied or blocked by a therapeutic moiety, as described below, to confer functionality on the metal ion complex. Thus, for example, Gd(III) may have 8 strongly associated coordination atoms or ligands and is capable of weakly binding a ninth ligand. Accordingly, suitable chelators for Gd(III) will have less than 9 coordination atoms. In a preferred embodiment, a Gd(III) chelator will have 8 coordination atoms, with a therapeutic blocking moiety either occupying or blocking the remaining site in the metal ion complex. In an alternative embodiment, the chelators used in the metal ion complexes of the invention have two less coordination atoms (n−2) than the metal ion is capable of binding (n), with these coordination sites occupied by one or more therapeutic blocking moieties. Thus, alternative embodiments utilize Gd(III) chelators with at least 5 coordination atoms, with at least 6 coordination atoms being preferred, at least 7 being particularly preferred, and at least 8 being especially preferred, with the therapeutic blocking moiety either occupying or blocking the remaining sites. It should be appreciated that the exact structure of the chelator and therapeutic blocking moiety may be difficult to determine, and thus the exact number of coordination atoms may be unclear. For example, it is possible that the chelator provide a fractional or non-integer number of coordination atoms; i.e. the chelator may provide 7.5 coordination atoms, i.e. the 8th coordination atom is on average not fully bound to the metal ion. However, the metal ion complex may still be functional, if the 8th coordination atom is sufficiently bound to prevent the rapid exchange of water at the site, and/or the therapeutic blocking moiety impedes the rapid exchange of water at the site.

There are a large number of known macrocyclic chelators or ligands which are used to chelate lanthanide and paramagnetic ions. See for example, Alexander, Chem. Rev. 95:273–342 (1995) and Jackels, Pharm. Med. Imag, Section III, Chap. 20, p645 (1990), expressly incorporated herein by reference, which describes a large number of macrocyclic chelators and their synthesis. Similarly, there are a number of patents which describe suitable chelators for use in the invention, including U.S. Pat. Nos. 5,155,215, 5,087,440, 5,219,553, 5,188,816, 4,885,363, 5,358,704, 5,262,532, and Meyer et al., Invest. Radiol. 25: S53 (1990), all of which are also expressly incorporated by reference. Thus, as will be understood by those in the art, any of the known paramagnetic metal ion chelators or lanthanide chelators can be easily modified using the teachings herein to further comprise at least one therapeutic blocking moiety.

When the metal ion is Gd(III), a preferred chelator is 1,4,7,10-tetraazacyclododecane-N,N',N", N'''-tetracetic acid (DOTA) or substituted DOTA. DOTA has the structure shown below:

Structure 1

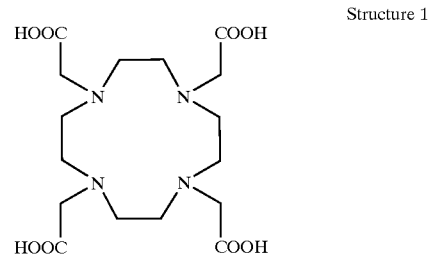

By "substituted DOTA" herein is meant that the DOTA may be substituted at any of the following positions, as shown below:

Structure 2

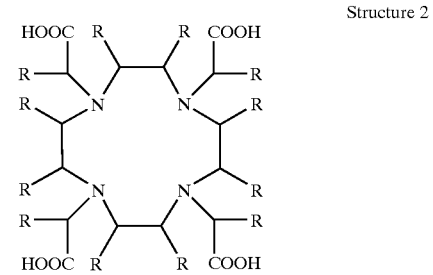

Suitable R substitution groups include a wide variety of groups, as will be understood by those in the art and as defined below. For example, suitable substitution groups include substitution groups disclosed for DOTA and DOTA-type compounds in U.S. Pat. Nos. 5,262,532, 4,885,363, and 5,358,704. These groups include hydrogen, alkyl groups including substituted alkyl groups and heteroalkyl groups, aryl groups including substituted aryl and heteroaryl groups, halogens such as chlorine, bromine and fluorine; amines; amides; esters; ethers; glycols, including ethylene glycols; hydroxy groups; aldehydes; alcohols; carboxylic acids; nitro groups; sulfonyl; silicon moieties; sulfur containing moieties; phosphorus containing moieties; carbonyl groups; targeting moieties; therapeutic blocking moieties and chemical functional groups. As will be appreciated by those skilled in the art, each position designated above may have two R groups attached (R' and R" ), although in a preferred embodiment only a single non-hydrogen R group is attached at any particular position; that is, preferably at least one of the R groups at each position is hydrogen. Thus, if R is an alkyl or aryl group, there is generally an additional hydrogen attached to the carbon, although not depicted herein. In a preferred embodiment, one R group is a therapeutic blocking moiety and the other R groups are hydrogen.

By "alkyl group" or grammatical equivalents herein is meant a straight or branched chain alkyl group, with straight chain alkyl groups being preferred. If branched, it may be branched at one or more positions, and unless specified, at any position. Also included within the definition of alkyl are heteroalkyl groups, wherein the heteroatom is selected from nitrogen, oxygen, phosphorus, sulfur and silicon. Also included within the definition of an alkyl group are cycloalkyl groups such as C5 and C6 rings, and heterocycloalkyl.

Additional suitable heterocyclic substituted rings are depicted in U.S. Pat. No. 5,087,440, expressly incorporated by reference. In some embodiments, two adjacent R groups may be bonded together to form ring structures together with the carbon atoms of the chelator, such as is described in U.S. Pat. No. 5,358,704, expressly incorporated by reference. These ring structures may be similarly substituted.

The alkyl group may range from about 1 to 20 carbon atoms (C1–C20), with a preferred embodiment utilizing from about 1 to about 10 carbon atoms (C1–C10), with about C1 through about C5 being preferred. However, in some embodiments, the alkyl group may be larger, for example when the alkyl group is the coordination site barrier.

By "alkyl amine" or grammatical equivalents herein is meant an alkyl group as defined above, substituted with an amine group at any position. In addition, the alkyl amine may have other substitution groups, as outlined above for alkyl group. The amine may be primary (—NH$_2$R), secondary (—NHR$_2$), or tertiary (—NR$_3$). When the amine is a secondary or tertiary amine, suitable R groups are alkyl groups as defined above. A preferred alkyl amine is p-aminobenzyl. When the alkyl amine serves as the coordination site barrier, as described below, preferred embodiments utilize the nitrogen atom of the amine as a coordination atom, for example when the alkyl amine includes a pyridine or pyrrole ring.

By "aryl group" or grammatical equivalents herein is meant aromatic aryl rings such as phenyl, heterocyclic aromatic rings such as pyridine, furan, thiophene, pyrrole, indole and purine, and heterocyclic rings with nitrogen, oxygen, sulfur or phosphorus.

Included within the definition of "alkyl" and "aryl" are substituted alkyl and aryl groups. That is, the alkyl and aryl groups may be substituted, with one or more substitution groups. For example, a phenyl group may be a substituted phenyl group. Suitable substitution groups include, but are not limited to, halogens such as chlorine, bromine and fluorine; amines; amides; esters; ethers; glycols, including ethylene glycols; hydroxy groups; aldehydes; alcohols; carboxylic acids; nitro groups; sulfonyl; silicon moieties; sulfur containing moieties; phosphorus containing moieties; carbonyl and other alkyl and aryl groups as defined herein, targeting moieties, therapeutic blocking moieties and chemical functional groups. Thus, arylalkyl and hydroxyalkyl groups are also suitable for use in the invention. Preferred substitution groups include alkyl amines and alkyl hydroxy.

By "phosphorus containing moieties" herein is meant compounds containing phosphorus, including, but not limited to, phosphines and phosphates, including the —PO(OH)(R$_{25}$)$_2$ group. The phosphorus may be an alkyl phosphorus; for example, DOTEP utilizes ethylphosphorus as a substitution group on DOTA. R$_{25}$ may be alkyl, substituted alkyl, hydroxy. A preferred embodiment has a —PO(OH)$_2$R$_{25}$ group.

By "amino groups" or grammatical equivalents herein is meant —NH$_2$, —NHR and —NR$_2$ groups, with R being as defined herein.

By "nitro group" herein is meant an —NO$_2$ group.

By "sulfur containing moieties" herein is meant compounds containing sulfur atoms, including but not limited to, thia-, thio- and sulfo-compounds, thiols (—SH and —SR), and sulfides (—RSR—).

By "silicon containing moieties" herein is meant compounds containing silicon.

By "ether" herein is meant an —O—R group. Preferred ethers include alkoxy groups, with —O—(CH$_2$)$_2$CH$_3$ and —O—(CH$_2$)$_4$CH$_3$ being preferred.

By "ester" herein is meant a —COOR group.

By "halogen" herein is meant bromine, iodine, chlorine, or fluorine. Preferred substituted alkyls are partially or fully halogenated alkyls such as CF$_3$, etc.

By "aldehyde" herein is meant —RCOH groups.

By "alcohol" herein is meant —OH groups, and alkyl alcohols —ROH.

By "amido" herein is meant —RCONH— or RCONR— groups.

By "ethylene glycol" or "(poly)ethylene glycol" herein is meant a —(O—CH$_2$—CH$_2$)$_n$— group, although each carbon atom of the ethylene group may also be singly or doubly substituted, i.e. —(O—CR$_2$—CR$_2$)$_n$—, with R as described above. Ethylene glycol derivatives with other heteroatoms in place of oxygen (i.e. —(N—CH$_2$—CH$_2$)$_n$— or —(S—CH$_2$—Ch$_2$)$_n$—, or with substitution groups) are also preferred.

By the term "targeting moiety" herein is meant a functional group that serves to target or direct the complex to a particular location or association, i.e. a specific binding event. Thus, for example, a targeting moiety may be used to target a molecule to a specific target protein or enzyme, or to a particular cellular location, or to a particular cell type. Suitable targeting moieties include, but are not limited to, polypeptides, nucleic acids, carbohydrates, lipids, hormones including proteinaceous and steroid hormones, growth factors, receptor ligands, antigens and antibodies, and the like. For example, as is more fully outlined below, a therapeutically active agent such as the cobalt compounds outlined below may include a targeting moiety to specifically bind a particular protein. Alternatively, as is more fully outlined below, the MRI agents of the invention may include a targeting moiety to target the agents to a specific cell type such as tumor cells, such as a transferrin moiety, since many tumor cells have significant transferrin receptors on their surfaces. Similarly, a targeting moiety may include components useful in targeting the MRI agents or the therapeutically active agents (if released) to a particular subcellular location. As will be appreciated by those in the art, the localization of proteins within a cell is a simple method for increasing effective concentration. For example, shuttling a drug into the nucleus confines them to a smaller space thereby increasing concentration. Finally, the physiological target may simply be localized to a specific compartment, and the drugs must be localized appropriately.

Thus, suitable targeting sequences include, but are not limited to, binding sequences capable of causing binding of the moiety to a predetermined molecule or class of molecules while retaining bioactivity of the expression product, (for example by using enzyme inhibitor or substrate sequences to target a class of relevant enzymes); sequences signaling selective degradation, of itself or co-bound proteins; and signal sequences capable of constitutively localizing the candidate expression products to a predetermined cellular locale, including a) subcellular locations such as the Golgi, endoplasmic reticulum, nucleus, nucleoli, nuclear membrane, mitochondria, chloroplast, secretory vesicles, lysosome, and cellular membrane; and b) extracellular locations via a secretory signal. Particularly preferred is localization to either subcellular locations.

Another class of suitable substitution groups are chemical functional groups that are used to add the components of the invention together, as is more fully outlined below. Thus, in general, the components of the invention are attached through the use of functional groups on each that can then be used for attachment. Preferred functional groups for attachment are amino groups, carboxy groups, oxo groups and thiol groups. These functional groups can then be attached, either directly or indirectly through the use of a linker. Linkers are well known in the art; for example, homo-or hetero-bifunctional linkers as are well known (see 1994 Pierce Chemical Company catalog, technical section on cross-linkers, pages 155–200, incorporated herein by reference). Preferred linkers include, but are not limited to, alkyl groups (including substituted alkyl groups and alkyl groups containing heteroatom moieties), with short alkyl groups, esters, amide, amine, epoxy groups, nucleic acids, peptides and ethylene glycol and derivatives being preferred.

The substitution group may also be hydrogen or a therapeutic blocking moiety, as is described below.

In an alternative embodiment, when the metal ion is Gd(III), a preferred chelator is diethylenetriaminepentaacetic acid (DTPA) or substituted DTPA. DPTA has the structure shown below:

Structure 3

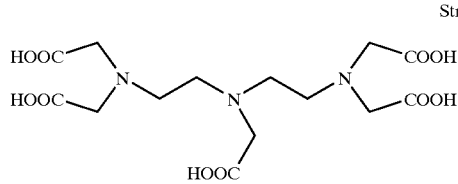

By "substituted DPTA" herein is meant that the DPTA may be substituted at any of the following positions, as shown below:

Structure 4

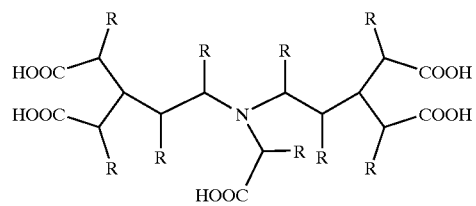

See for example U.S. Pat. No. 5,087,440.

Suitable R substitution groups include those outlined above for DOTA. Again, those skilled in the art will appreciate that there may be two R groups (R' and R" ) at each position designated above, although as described herein, at least one of the groups at each position is hydrogen, which is generally not depicted herein.

In an alternative embodiment, when the metal ion is Gd(III), a preferred chelator is 1,4,7,10-tetraazacyclododecane-N,N',N",N'''-tetraethylphosphorus (DOTEP) or substituted DOTEP (see U.S. Pat. No. 5,188,816). DOTEP has the structure shown below:

Structure 5

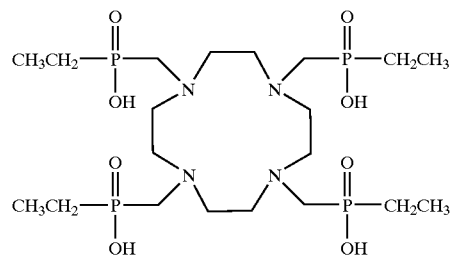

DOTEP may have similar R substitution groups as outlined above.

Other suitable Gd(III) chelators are described in Alexander, supra, Jackels, supra, U.S. Pat. Nos. 5,155,215, 5,087,440, 5,219,553, 5,188,816, 4,885,363, 5,358,704, 5,262,532, and Meyer et al., Invest. Radiol. 25: S53 (1990), among others.

When the paramagnetic ion is Fe(III), appropriate chelators will have less than 6 coordination atoms, since Fe(III) is capable of binding 6 coordination atoms. Suitable chelators for Fe(III) ions are well known in the art, see for example Lauffer et al., J. Am. Chem. Soc. 109:1622 (1987); Lauffer, Chem. Rev. 87:901–927 (1987); and U.S. Pat. Nos. 4,885,363, 5,358,704, and 5,262,532, all which describe chelators suitable for Fe(III).

When the paramagnetic ion is Mn(II) (Mn+2), appropriate chelators will have less than 5 or 6 coordination atoms, since Mn(II) is capable of binding 6 or 7 coordination atoms. Suitable chelators for Mn(II) ions are well known in the art; see for example Lauffer, Chem. Rev. 87:901–927 (1987) and U.S. Pat. Nos. 4,885,363, 5,358,704, and 5,262,532.

When the paramagnetic ion is Yt(III), appropriate chelators will have less than 7 or 8 coordination atoms, since Yt(III) is capable of binding 8 or 9 coordination atoms. Suitable chelators for Yt(III) ions include, but are not limited to, DOTA and DPTA and derivatives thereof (see Moi et al., J. Am. Chem. Soc. 110:6266–6267 (1988)) and those chelators described in U.S. Pat. No. 4,885,363 and others, as outlined above.

When the paramagnetic ion is Dy+3 (Dy(III)), appropriate chelators will have less than 7 or 8 coordination atoms, since Dylll is capable of binding 8 or 9 coordination atoms. Suitable chelators are known in the art, as above.

In a preferred embodiment, the chelator and the therapeutic blocking moiety are covalently linked; that is, the therapeutic blocking moiety is a substitution group on the chelator. In this embodiment, the substituted chelator, with the bound metal ion, comprises the metal ion complex which in the absence of the target substance has all possible coordination sites occupied or blocked; i.e. it is coordinatively saturated.

In an alternative embodiment, the chelator and the therapeutic blocking moiety are not covalently attached. In this embodiment, the therapeutic blocking moiety has sufficient affinity for the metal ion to prevent the rapid exchange of water molecules in the absence of the target substance. However, in this embodiment the therapeutic blocking moiety has a higher affinity for the target substance than for the metal ion. Accordingly, in the presence of either a cleavage agent or the physiological target, the therapeutic blocking moiety will have a tendency to be dislodged from the metal ion to interact with the target substance, thus freeing up a coordination site in the metal ion complex and allowing the rapid exchange of water and an increase in relaxivity.

What is important is that the metal ion complex, comprising the metal ion, the chelator and the therapeutic blocking moiety, is not readily able to rapidly exchange water molecules when the therapeutic moeities are in the inner coordination sphere of the metal ion, such that in the presence of the therapeutic blocking moiety, there is less or little substantial image enhancement.

By "therapeutic blocking moiety" or grammatical equivalents herein is meant a moiety with several essential functions. First, some component of the therapeutic blocking moiety must be capable of substantially inhibiting the exchange of water in at least one inner coordination site of the metal ion of the metal ion complex. Second, some component of the therapeutic blocking moiety must be capable of effecting a therapeutic effect, i.e. altering the function of its physiological target substance. In addition, a further requirement is that as a result of either the interaction of the therapeutic blocking moiety with the physiological target substance or as a result of the action of a separate enzyme such as a protease on a cleavage site present in the therapeutic blocking moiety, the exchange of water in at least one inner coordination site of the metal ion is increased. As is more fully described below, this is generally done as a result of a cleavage of some or all of the therapeutic blocking moiety off the chelator, although other types of interactions can be utilized as well. As is more fully described below, each of these functions may be accomplished by a single component, or multiple components are used, together forming the therapeutic blocking moiety. That is, for example, the therapeutically active agent may provide the coordination atom(s). Furthermore, as is more fully outlined below, the therapeutic blocking moiety may comprise a targeting moiety to allow targeting of the drug moiety to a particular target. Finally, therapeutic blocking moieties may comprise one or more linker groups to allow for correct spacing and attachment of the components of the therapeutic blocking moiety as needed.

Accordingly, a therapeutic blocking moiety can comprise one or more several components, as outlined herein. At a minimum, a therapeutic blocking moiety comprises a "therapeutically active agent" or "drug moiety" capable of causing a therapeutic effect, that is, it alters a biological function of a physiological target substance. As outlined below, this drug moiety may or may not provide the coordination atom(s) of the therapeutic blocking moiety. By "causing a therapeutic effect" or "therapeutically effective" or grammatical equivalents herein is meant that the drug alters the biological function of its intended physiological target in a manner sufficient to cause a therapeutic and phenotypic effect. By "alters" or "modulates the biological function" herein is meant that the physiological target undergoes a change in either the quality or quantity of its biological activity; this includes increases or decreases in activity. Thus, therapeutically active agents include a wide variety of drugs, including antagonists, for example enzyme inhibitors, and agonists, for example a transcription factor which results in an increase in the expression of a desirable gene product (although as will be appreciated by those in the art, antagonistic transcription factors may also be used), are all included.

In a preferred embodiment, the therapeutically active agent is cleaved from the MRI agent, as is more fully described below. In this embodiment, as a result of cleavage of the therapeutic blocking moiety and the release of the therapeutically active agent, a coordination site of the MRI agent is no longer occupied by a coordination atom and water is free to exchange in this site, leading to signal enhancement. Furthermore, the drug is now free to interact with its target, which may or may not be the same molecule which does the cleavage; for example, the cleavage site may comprise an enzyme substrate, for example of an HIV protease, and the drug may comprise an inhibitor of the same enzyme. Accordingly, in this embodiment, the nature of the interaction is irreversible; the coordination atom released from the MRI agent does not reassociate to block or occupy the coordination site. This embodiment allows the amplification of the image enhancement since a single cleavage agent leads to the generation of many activated metal ion complexes, i.e. metal ion complexes in which the therapeutic blocking moiety is no longer occupying or blocking a coordination site of the metal ion.

In an alternate embodiment, the therapeutically active agent need not be cleaved from the MRI agent to be active. Thus, for example, as is more fully outlined below, some agents can remain associated with the MRI agent; what is important in this instance is that the association of the drug with its target causes a conformational alteration that results in a coordination site, originally occupied by a coordination atom from the therapeutic blocking moiety, to become vacated, allowing an increase in the exchange of water and thus image enhancement. That is, the affinity of the drug for its target is greater than the affinity of the therapeutic blocking moiety for the MRI agent. Depending on the nature of the interaction of the drug with its physiological target, this may or may not be a reversible interaction. That is, in some cases, for example in the case of certain enzyme inhibitors, the interaction is effectively irreversible, leading to an enzyme active site being occupied with a drug attached to an MRI agent. Alternatively, in some embodiments, the interaction is reversible, and an equilibrium is established between having the drug associated with its target (leading to image enhancement) and having the therapeutic blocking moiety associated with the MRI agent (hindering the exchange of water and thus a loss of signal).

The nature of the therapeutic effect between the therapeutically active moiety and the physiological target substance will depend on the both the physiological target substance and the nature of the effect. In general, suitable physiological target substances include, but are not limited to, proteins (including peptides and oligopeptides) including ion channels and enzymes; nucleic acids; ions such as Ca+2, Mg+2, Zn+2, K+, Cl−, Na+, and toxic ions including those of Fe, Pb, Hg and Se; cAMP; receptors including G-protein coupled receptors and cell-surface receptors and ligands; hormones; antigens; antibodies; ATP; NADH; NADPH; $FADH_2$; $FNNH_2$; coenzyme A (acyl CoA and acetyl CoA); and biotin, among others. Physiological target substances include enzymes and proteins associated with a wide variety of viruses including orthomyxoviruses, (e.g. influenza virus), paramyxoviruses (e.g respiratory syncytial virus, mumps virus, measles virus), adenoviruses, rhinoviruses, coronaviruses, reoviruses, togaviruses (e.g. rubella virus), parvoviruses, poxviruses (e.g. variola virus, vaccinia virus), enteroviruses (e.g. poliovirus, coxsackievirus), hepatitis viruses (including A, B and C), herpesviruses (e.g. Herpes simplex virus, varicella-zoster virus, cytomegalovirus, Epstein-Barr virus), rotaviruses, Norwalk viruses, hantavirus, arenavirus, rhabdovirus (e.g. rabies virus), retroviruses (including HIV, HTLV-I and -II), papovaviruses (e.g. papillomavirus), polyomaviruses, and picornaviruses, and the like. Similarly, bacterial targets can come from a wide variety of pathogenic and non-pathogenic prokaryotes of interest including Bacillus; Vibrio, e.g. *V. cholerae*; Escherichia, e.g. Enterotoxigenic *E. coli*, Shigella, e.g. *S. dysenteriae*; Salmonella, e.g. *S. typhi*; Mycobacterium e.g. *M. tuberculosis, M. leprae*; Clostridium, e.g. *C. botulinum, C. tetani, C. difficile, C.perfringens*; Cornyebacterium, e.g. *C. diphtheriae*; Streptococcus, *S. pyogenes, S. pneumoniae*; Staphylococcus, e.g. *S. aureus*; Haemophilus, e.g. *H. influenzae*; Neisseria, e.g. *N. meningitidis, N. gonorrhoeae*; Yersinia, e.g. *G. lamblia, Y. pestis*, Pseudomonas, e.g. *P. aeruginosa, P. putida*; Chlamydia, e.g. *C. trachomatis*; Bordetella, e.g. *B. pertussis*; Treponema, e.g. *T. palladium*; and the like.

Once the physiological target substance has been identified, a corresponding therapeutically active agent is chosen. These agents will be any of a wide variety of drugs, including, but not limited to, enzyme inhibitors, hormones, cytokines, growth factors, receptor ligands, antibodies, antigens, ion binding compounds including crown ethers and other chelators, substantially complementary nucleic acids, nucleic acid binding proteins including transcription factors, toxins, etc. Suitable drugs include cytokines such as erythropoietin (EPO), thrombopoietin (TPO), the interleukins (including IL-1 through IL-17), insulin, insulin-like growth factors (including IGF-1 and -2), epidermal growth factor (EGF), transforming growth factors (including TGF-α and TGF-β), human growth hormone, transferrin, epidermal growth factor (EGF), low density lipoprotein, high density lipoprotein, leptin, VEGF, PDGF, ciliary neurotrophic factor, prolactin, adrenocorticotropic hormone (ACTH), calcitonin, human chorionic gonadotropin, cotrisol, estradiol, follicle stimulating hormone (FSH), thyroid-stimulating hormone (TSH), leutinzing hormone (LH), progeterone, testosterone, toxins including ricin, and any drugs as outlined in the Physician's Desk Reference, Medical Economics Data Production Company, Montvale, N.J., 1998.

In a preferred embodiment, the physiological target is a protein that contains a histidine residue that is important for the protein's bioactivity. In this case, the therapeutically active agent can be a metal ion complex (not to be confused with the metal ion complex of the MRI agent), such as is generally described in PCT US95/16377, PCT US95/16377, PCT US96/19900, PCT US96/15527, and references cited within, all of which are expressly incorporated by reference. These complexes take on the general structure outlined below, and have been shown to be efficacious in decreasing the bioactivity of proteins, particularly enzymes, with a biologically important histidine residue. These cobalt complexes appear to derive their biological activity by the substitution or addition of ligands in the axial positions. The biological activity of these compounds results from the binding of a new axial ligand, most preferably the nitrogen atom of imidazole of the side chain of histidine which is required by the target protein for its biological activity. Thus, proteins such as enzymes that utilize a histidine in the active site, or proteins that use histidine, for example, to bind essential metal ions, can be inactivated by the binding of the histidine in an axial ligand position of the cobalt compound, thus preventing the histidine from participating in its normal biological function.

Structure 6

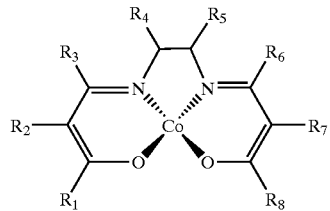

In Structure 6, the metal ion is shown as Co, which may be either Co(II) or Co(III) or other tetradentate metal ions, including Fe, Au and Cr (see PCT US96/15527). Each of $R_1$, $R_2$, $R_3$, $R_4$, $R_5$, $R_6$, $R_7$ an $R_8$ is a substitution group as defined herein, with hydrogen, alkyl, aryl, or targeting moieties being preferred. In general, at least one of the R groups will include a chemical functional group for the attachment of the cobalt complex to the remainder of the MRI agent.

In a preferred embodiment, the physiological target protein is an enzyme. As will be appreciated by those skilled in the art, the possible enzyme target substances are quite broad. Suitable classes of enzymes include, but are not limited to, hydrolases such as proteases, carbohydrases, lipases and nucleases; isomerases such as racemases, epimerases, tautomerases, or mutases; transferases, kinases and phophatases. Enzymes associated with the generation or maintenance of arterioschlerotic plaques and lesions within the circulatory system, inflammation, wounds, immune response, tumors, apoptosis, exocytosis, etc. may all be treated using the present invention. Enzymes such as lactase, maltase, sucrase or invertase, cellulase, α-amylase, aldolases, glycogen phosphorylase, kinases such as hexokinase, proteases such as serine, cysteine, aspartyl and metalloproteases may also be detected, including, but not limited to, trypsin, chymotrypsin, and other therapeutically relevant serine proteases such as tPA and the other proteases of the thrombolytic cascade; cysteine proteases including: the cathepsins, including cathepsin B, L, S, H, J, N and O; and calpain; and caspases, such as caspase−3, −5, −8 and other caspases of the apoptotic pathway, such as interleukin-converting enzyme (ICE). Similarly, bacterial and viral infections may be detected via characteristic bacterial and viral enzymes. As will be appreciated in the art, this list is not meant to be limiting.

Once the target enzyme is identified or chosen, enzyme inhibitor therapeutically active agents can be designed using well known parameters of enzyme substrate specificities. As outlined above, the inhibitor may be another metal ion complex such as the cobalt complexes described above. Other suitable enzyme inhibitors include, but are not limited to, the cysteine protease inhibitors described in PCT US95/02252, PCT/US96/03844 and PCT/US96/08559, and known protease inhibitors that are used as drugs such as inhibitors of HIV proteases.

In one embodiment, the therapeutically active agent is a nucleic acid, for example to do gene therapy or antisense therapy. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169–176). Several nucleic acid analogs are described in Rawls, C & E News Jun. 2, 1997 page 35. All of these references are hereby expressly incorporated by reference. These modifications of the ribose-phosphate backbone may be done to increase the stability and half-life of such molecules in physiological environments; for example, PNA antisense embodiments are particularly preferred.

As will be appreciated by those in the art, all of these nucleic acid analogs may find use in the present invention. In addition, mixtures of naturally occurring nucleic acids and analogs can be made or mixtures of different nucleic acid analogs.

The nucleic acid may be single-stranded or double stranded. The physiological target molecule can be a substantially complementary nucleic acid or a nucleic acid binding moiety, such as a protein.

In a preferred embodiment, the physiological target substance is a physiologically active ion, and the therapeutically active agent is an ion binding ligand or chelate. For example, toxic metal ions could be chelated to decrease toxicity, using a wide variety of known chelators including, for example, crown ethers.

In addition to the therapeutically active agent, a therapeutic blocking moiety may include other components. As outlined herein, a preferred embodiment provides that coordination atom(s) for the metal ion are provided by the therapeutically active agent. However, if the therapeutically active agent does not contribute a coordination atom, the therapeutic blocking moiety further comprises a "coordination site barrier" which is covalently tethered to the complex in such a manner as to allow disassociation upon delivery of the therapeutically active agent. For example, it may be tethered by one or more enzyme substrate cleavage sites. In this embodiment, the coordination site barrier blocks or occupies at least one of the coordination sites of the metal ion in the absence of the target substance. Coordination site barriers are used when coordination atoms are not provided by the other components of the MRI agents, i.e. the therapeutically active agents, the cleavage site(s), the targeting moiety, linkers, etc. The other components of the therapeutic blocking moiety such as an enzyme cleavage site serves as the tether, covalently linking the coordination site barrier to the metal ion complex. As a result of either a cleavage or a conformation change due to the interaction of the therapeutically active agent with its physiological target, the coordination site or sites are no longer blocked and the bulk water is free to rapidly exchange at the coordination site of the metal ion, thus enhancing the image.

In one embodiment, the coordination site barrier is attached to the metal ion complex at one end, as is depicted in FIGS. 2A and 2B. FIG. 2A depicts the case where an enzyme cleaves at the cleavage point, thereby releasing the coordination site barrier. FIG. 2B depicts the case wherein it is a conformational change as a result of the interaction of the drug with its physiological target that leads to the removal of the coordination site barrier. In another embodiment, the coordination site barrier is attached to the metal ion complex with more than one cleavage site, as is depicted in FIG. 2C for two attachments. The enzyme target may cleave only one side, thus removing the coordination site barrier and allowing the exchange of water at the coordination site, but leaving the coordination site barrier attached to the metal ion complex. Alternatively, the enzyme may cleave the coordination site barrier completely from the metal ion complex.

In a preferred embodiment, the coordination site barrier occupies at least one of the coordination sites of the metal ion. That is, the coordination site barrier contains at least one atom which serves as at least one coordination atom for the metal ion. In this embodiment, the coordination site barrier may be a heteroalkyl group, such as an alkyl amine group, as defined above, including alkyl pyridine, alkyl pyrroline, alkyl pyrrolidine, and alkyl pyrole, or a carboxylic or carbonyl group. The portion of the coordination site barrier which does not contribute the coordination atom may also be considered a linker group.

In an alternative embodiment, the coordination site barrier does not directly occupy a coordination site, but instead blocks the site sterically. This may also be true for the therapeutically active agents. In this embodiment, the coordination site barrier may be an alkyl or substituted group, as defined above, or other groups such as peptides, proteins, nucleic acids, etc.

In this embodiment, the coordination site barrier is preferably linked via two enzyme substrates to opposite sides of the metal ion complex, effectively "stretching" the coordination site barrier over the coordination site or sites of the metal ion complex, as is depicted in FIG. 2C.

In some embodiments, the coordination site barrier may be "stretched" via an enzyme substrate on one side, covalently attached to the metal ion complex, and a linker moiety, as defined below, on the other. In an alternative embodiment, the coordination site barrier is linked via a single enzyme substrate on one side; that is, the affinity of the coordination site barrier for the metal ion is higher than that of water, and thus the therapeutic blocking moiety, comprising the coordination site barrier and the enzyme substrate, will block or occupy the available coordination sites in the absence of the target enzyme.

In addition to the therapeutically active agents and coordination site barriers, a therapeutic blocking moiety may also comprise a cleavage site. As described herein, one way of delivering the therapeutically active agent is to cleave it off the MRI agent. It is also possible to configure the MRI agents of the invention such that a coordination site barrier is cleaved off, leaving the therapeutically active agent attached to the MRI agent, but in a conformation wherein the drug is now able to interact with its target in a way it was not able to prior to cleavage as is generally depicted in FIG. 1C. In some embodiments, the coordination atom(s) that hinder the rapid exchange of water at a coordination site may be contributed by the cleavage site. Thus for example, when a proteolytic cleavage site is used, coordination atoms may be provided by an atom of the peptide chain.

In a preferred embodiment, the physiological target is an enzyme and the cleavage site corresponds to that enzyme. Alternatively, the cleavage site is unrelated to the physiological target. In this embodiment, the cleavage site may be either specific to a disease condition, for example the cleavage site may be an HIV protease site and the therapeutically active agent is chosen to interfere with a different viral function (for example viral replication), or it may be non-specific, relying instead on a different mechanism for specificity, if desired. For example, the cleavage site may be a "generic" intracellular protease site, and specificity can be provided by a targeting moiety attached to the MRI agent; for example, a cell-specific ligand could be used to target a specific set of cells such as tumor cells.

Thus, for example, a proteolytic cleavage site may be used for cleavage by proteases. The cleavage site thus comprises a peptide or polypeptide that is capable of being cleaved by a defined protease. By "peptide" or "polypeptide" herein is meant a compound of about 2 to about 15 amino acid residues covalently linked by peptide bonds. Preferred embodiments utilize polypeptides from about 2 to about 8 amino acids, with about 2 to about 4 being the most preferred. Preferably, the amino acids are naturally occurring amino acids, although amino acid analogs and peptidomimitic structures are also useful. Under certain circumstances, the peptide may be only a single amino acid residue.

Similarly, when the enzyme is a carbohydrase, the cleavage site will be a carbohydrate group which is capable of being cleaved by the target carbohydrase. For example, when the enzyme is lactase or β-galactosidase, the cleavage site is lactose or galactose. Similar pairs include sucrase/sucrose, maltase/maltose, and α-amylase/amylose.

In a preferred embodiment, the cleavage site is a phosphorus moiety, as defined above, such as —(OPO(OR$_2$))$_n$, wherein n is an integer from 1 to about 10, with from 1 to 5 being preferred and 1 to 3 being particularly preferred.

Each R is independently hydrogen or a substitution group as defined herein, with hydrogen being preferred. This embodiment is particularly useful when the cleavage enzyme is alkaline phosphatase or a phosphodiesterase, or other enzymes known to cleave phosphorus containing moieties such as these.

In a preferred embodiment, the cleavage site utilizes a photocleavable moiety. That is, upon exposure to a certain wavelength of light, cleavage occurs, allowing an increase in the exchange rate of water in at least one coordination site of the complex. This embodiment has particular use in developmental biology fields (cell lineage, neuronal development, etc.), where the ability to follow the fates of particular cells is desirable. Suitable photocleavable moieties are similar to "caged" reagents which are cleaved upon exposure to light. A particularly preferred class of photocleavable moieties are the O-nitrobenzylic compounds, which can be synthetically incorporated into a therapeutic blocking moiety via an ether, thioether, ester (including phosphate esters), amine or similar linkage to a heteroatom (particularly oxygen, nitrogen or sulfur). Also of use are benzoin-based photocleavable moieties. A wide variety of suitable photocleavable moieties is outlined in the Molecular Probes Catalog, supra.

In a preferred embodiment, a photocleavable site has a structure depicted below in Structure 7, which depicts a nitrobenzyl photocleavable group, although as will be appreciated by those in the art, a wide variety of other moieties may be used:

Structure 7

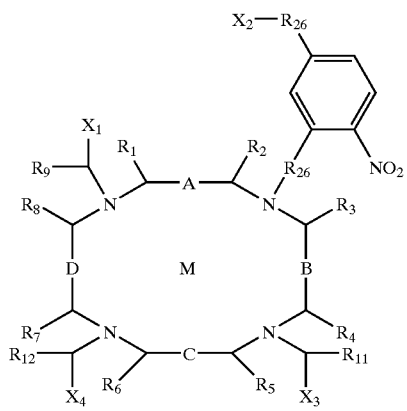

Structure 7 depicts a DOTA-type chelator, although as will be appreciated by those in the art, other chelators may be used as well. $R_{26}$ is a linker as defined herein. The $X_2$ group includes the other components of the therapeutic blocking moiety, including a therapeutically active agent and an optional coordination site barrier. Similarly, there may be substitutent groups on the aromatic ring, as is known in the art.

In addition to the components outlined above, it should be appreciated that the therapeutic blocking moieties of the present invention may further comprise a linker group as well as a functional therapeutic blocking moiety. Again, as outlined herein for the therapeutically active agents and the cleavage sites, a coordination atom may actually be provided by the linker.

Linker groups (sometimes depicted herein as $R_{26}$) will be used to optimize the steric considerations of the metal ion complex. That is, in order to optimize the interaction of the therapeutic blocking moiety with the metal ion, linkers may be introduced to allow the coordination site to-be blocked. In general, the linker group is chosen to allow a degree of structural flexibility. For example, when a therapeutically active agent interacts with its physiological target in a manner that does not result in the therapeutically active agent being cleaved from the complex, the linker must allow some movement of the therapeutically active agent away from the complex, such that the exchange of water at at least one coordination site is increased.

Generally, suitable linker groups include, but are not limited to, alkyl and aryl groups, including substituted alkyl and aryl groups and heteroalkyl (particularly oxo groups) and heteroaryl groups, including alkyl amine groups, as defined above. Preferred linker groups include p-aminobenzyl, substituted p-aminobenzyl, diphenyl and substituted diphenyl, alkyl furan such as benzylfuran, carboxy, and straight chain alkyl groups of 1 to 10 carbons in length. Particularly preferred linkers include p-aminobenzyl, methyl, ethyl, propyl, butyl, pentyl, hexyl, acetic acid, propionic acid, aminobutyl, p-alkyl phenols, 4-alkylimidazole. The selection of the linker group is generally done using well known molecular modeling techniques, to optimize the obstruction of the coordination site or sites of the metal ion. In addition, the length of this linker may be very important in order to achieve optimal results.

Accordingly, the therapeutic blocking moieties of the invention include a therapeutically active agent and optional cleavage sites, coordination site barriers, and linkers, if required.

In some embodiments, the metal ion complexes of the invention have a single associated or bound therapeutic blocking moiety. In such embodiments, the single therapeutic blocking moiety impedes the exchange of water molecules in at least one coordination site. Alternatively, as is outlined below, a single therapeutic blocking moiety may hinder the exchange of water molecules in more than one coordination site.

In alternative embodiments, two or more therapeutic blocking moieties are associated with a single metal ion complex, to impede the exchange of water in at least one or more coordination sites.

The therapeutic blocking moiety is attached to the metal ion complex in a variety of ways, a small number of which are depicted in the Figures. In a preferred embodiment, as noted above, the therapeutic blocking moiety is attached to the metal ion complex via a linker group. Alternatively, the therapeutic blocking moiety is attached directly to the metal ion complex; for example, as outlined below, the therapeutic blocking moiety may be a substituent group on the chelator.

In a preferred embodiment at least one of the R groups attached to the "arms" of the chelator, for example $R_9$, $R_{10}$, $R_{11}$ or $R_{12}$ of the DOTA structures, or $R_{13}$, $R_{14}$, $R_{17}$, $R_{20}$ or $R_{21}$ of the DTPA structures, comprises an alkyl (including substituted and heteroalkyl groups), or aryl (including substituted and heteroaryl groups), i.e. is a group sterically bulkier than hydrogen. This is particular useful to drive the equilibrium towards "locking" the coordination atom of the arm into place to prevent water exchange, as is known for standard MRI contrast agents. Preferred groups include the C1 through C6 alkyl groups with methyl being particularly preferred.

This is particularly preferred when the therapeutic blocking moiety is attached via one of the "arms", for example when a therapeutic blocking moiety is at position $X_1$ to $X_4$ (Structure 8), or position H, I, J or K of Structure 9.

However the inclusion of too many groups may drive the equilibrium in the other direction effectively locking the coordination atom out of position. Therefore in a preferred embodiment only 1 or 2 of these positions is a non-hydrogen group, unless other methods are used to drive the equilibrium towards binding.

The therapeutic blocking moieties are chosen and designed using a variety of parameters. In the embodiment which uses a coordination site barrier and the coordination site barrier is fastened or secured on two sides, the affinity of the coordination site barrier of the therapeutic blocking moiety for the metal ion complex need not be great, since it is tethered in place. That is, in this embodiment, the complex is "off" in the absence of the cleavage agent. However, in the embodiment where the therapeutic blocking moiety is linked to the complex in such a manner as to allow some rotation or flexibility of the therapeutic blocking moiety, for example, it is linked on one side only, the therapeutic blocking moiety should be designed such that it occupies the coordination site a majority of the time.

When the therapeutic blocking moiety is not covalently tethered on two sides, it should be understood that the components of the therapeutic blocking moieties are chosen to maximize three basic interactions that allow the therapeutic blocking moiety to be sufficiently associated with the complex to hinder the rapid exchange of water in at least one coordination site of the complex. First, there may be electrostatic interactions between the therapeutic blocking moiety and the metal ion, to allow the therapeutic blocking moiety to associate with the complex. Secondly, there may be Van der Waals and dipole-dipole interactions. Thirdly, there may be ligand interactions, that is, one or more functionalities of the therapeutic blocking moiety may serve as coordination atoms for the metal. In addition, linker groups may be chosen to force or favor certain conformations, to drive the equilibrium towards an associated therapeutic blocking moiety. Similarly, removing degrees of fredom in the molecule may force a particular conformation to prevail. Thus, for example, the addition of alkyl groups, and particularly methyl groups, at positions equivalent to the $R_9$ to $R_{12}$ positions of Structure 6 when the therapeutic blocking moiety is attached at an "X" position can lead the therapeutic blocking moiety to favor the blocking position. Similar restrictions can be made in the other embodiments, as will be appreciated by those in the art.

Furthermore, effective "tethering" of the therapeutic blocking moiety down over the metal ion may also be done by engineering in other non-covalent interactions that will serve to increase the affinity of the therapeutic blocking moiety to the chelator complex, as is depicted below.

Potential therapeutic blocking moieties may be easily tested to see if they are functional; that is, if they sufficiently occupy or block the appropriate coordination site or sites of the complex to prevent rapid exchange of water. Thus, for example, complexes are made with potential therapeutic blocking moieties and then compared with the chelator without the therapeutic blocking moiety in imaging experiments. Once it is shown that the therapeutic blocking moiety is a sufficient "blocker", the experiments are repeated in the presence of either the physiological target (when it is the interaction of the target and the drug which causes either cleavage or a conformational change resulting in opening up of a coordination site) or the cleavage agent, to show an increase in the exchange of water and thus enhancement of the image.

Thus, as outlined above, the metal ion complexes of the present invention comprise a paramagnetic metal ion bound to a chelator and at least one therapeutic blocking moiety. In a preferrred embodiment, the metal ion complexes have the formula shown in Structure 8:

Structure 8

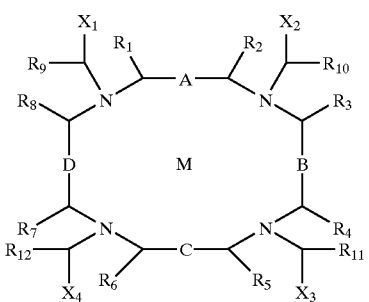

In Structure 8, M is a paramagnetic metal ion selected from the group consisting of Gd(III), Fe(III), Mn(II), Yt(III), and Dy(III). A, B, C and D are each either single or double bonds. The $R_1$ through $R_{12}$ groups are substitution groups as defined above, including therapeutic blocking moieties and targeting moieties. $X_1$ through $X_4$ are —OH, —COO—, —$(CH2)_n$OH (with —$CH_2$OH being preferred), —$(CH2)_n$COO— (with $CH_2$COO— being preferred), or a substitution group, including therapeutic blocking moieties and targeting moieties. n is from 1 to 10, with from 1 to 5 being preferred. At least one of $R_1$ to $R_{12}$ and $X_1$ to $X_4$ is a therapeutic blocking moiety.

In the Structures depicted herein, any or all of A, B, C or D may be a single bond or a double bond. It is to be understood that when one or more of these bonds are double bonds, there may be only a single substitutent group attached to the carbons of the double bond. For example, when A is a double bond, there may be only a single $R_1$ and a single $R_2$ group attached to the respective carbons; in a preferred embodiment, as described below, the $R_1$ and $R_2$ groups are hydrogen. In a preferred embodiment, A is a single bond, and it is possible to have two $R_1$ groups and two $R_2$ groups on the respective carbons. In a preferred embodiment, these groups are all hydrogen with the exception of a single therapeutic blocking moiety, but alternate embodiments utilize two R groups which may be the same or different. That is, there may be a hydrogen and a therapeutic group attached in the $R_1$ position, and two hydrogens, two alkyl groups, or a hydrogen and an alkyl group in the $R_2$ positions.

It is to be understood that the exact composition of the $X_1$–$X_4$ groups will depend on the presence of the metal ion. That is, in the absence of the metal ion, the groups may be —OH, —COOH, —$(CH_2)_n$OH, or $(CH_2)_n$COOH; however, when the metal is present, the groups may be —OH, —COO—, —$(CH_2)_n$O—, or $(CH_2)_n$COO—.

A further embodiment utilizes metal ion complexes having the formula shown in Structure 9:

Structure 9

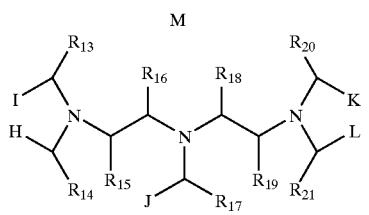

It is to be understood that, as above, the exact composition of the H, I, J, K and L groups will depend on the presence of the metal ion. That is, in the absence of the metal ion, H, I, J, K and L are —OH, —COOH, —$(CH_2)_n$OH, or $(CH_2)_n$COOH; however, when the metal is present, the groups are —OH, —COO—, —$(CH_2)_n$OH, or $(CH_2)_n$COO—.

In this embodiment, $R_{13}$ through $R_{21}$ are substitution groups as defined above. In a preferred embodiment, $R_{12}$ to $R_{21}$ are hydrogen. At least one of $R_{13}$–$R_{21}$, H, I, J, K or L is a therapeutic blocking moiety, as defined above.

In addition, the complexes and metal ion complexes of the invention may further comprise one or more targeting moieties. That is, a targeting moiety may be attached at any of the R positions (or to a linker or therapeutic blocking moiety, etc.), although in a preferred embodiment the targeting moiety does not replace a coordination atom.

In a preferred embodiment, the metal ion complexes of the present invention are water soluble or soluble in aqueous solution. By "soluble in aqueous solution" herein is meant that the MRI agent has appreciable solubility in aqueous solution and other physiological buffers and solutions. Solubility may be measured in a variety of ways. In one embodiment, solubility is measured using the United States Pharmacopeia solubility classifications, with the metal ion complex being either very soluble (requiring less than one part of solvent for 1 part of solute), freely soluble (requiring one to ten parts solvent per 1 part solute), soluble (requiring ten to thirty parts solvent per 1 part solute), sparingly soluble (requiring 30 to 100 parts solvent per 1 part solute), or slightly soluble (requiring 100–1000 parts solvent per 1 part solute).

Testing whether a particular metal ion complex is soluble in aqueous solution is routine, as will be appreciated by those in the art. For example, the parts of solvent required to solubilize a single part of MRI agent may be measured, or solubility in gm/ml may be determined.

The complexes of the invention are generally synthesized using well known techniques. See, for example, Moi et al., supra; Tsien et al., supra; Borch et al., J. Am. Chem. Soc., p2987 (1971); Alexander, (1995), supra; Jackels (1990), supra, U.S. Pat. Nos. 5,155,215, 5,087,440, 5,219,553, 5,188,816, 4,885,363, 5,358,704, 5,262,532 and 5,707,605; Meyer et al., (1990), supra, Moi et al., (1988), and McMurray et al., Bioconjugate Chem. 3(2):108–117 (1992)); see also PCT US95/16377, PCT US96/19900, and PCT US96/15527 all of which are expressly incorporated by reference.

For DOTA derivatives, the synthesis depends on whether nitrogen substitution or carbon substitution of the cyclen ring backbone is desired. For nitrogen substitution, the synthesis begins with cyclen or cyclen derivatives, as is well known in the art; see for example U.S. Pat. Nos. 4,885,363 and 5,358,704.

For carbon substitution, well known techniques are used. See for example Moi et al., supra, and Gansow, supra.

The contrast agents of the invention are complexed with the appropriate metal ion as is known in the art. While the structures depicted herein all comprise a metal ion, it is to be understood that the contrast agents of the invention need not have a metal ion present initially. Metal ions can be added to water in the form of an oxide or in the form of a halide and treated with an equimolar amount of a contrast agent composition. The contrast agent may be added as an aqueous solution or suspension. Dilute acid or base can be added if need to maintain a neutral pH. Heating at temperatures as high as 100° C. may be required.

The complexes of the invention can be isolated and purified, for example using HPLC systems.

Pharmaceutical compositions comprising pharmaceutically acceptable salts of the contrast agents can also be prepared by using a base to neutralize the complexes while they are still in solution. Some of the complexes are formally uncharged and do not need counterions.

In addition, the MRI agents of the invention can be added to polymers, using techniques generally outlined in PCT US95/14621 and U.S. Ser. No. 08/690,612 (allowed), both of which are expressly incorporated by reference. Briefly, chemical functional groups are added to the MRI agents to allow the chemical attachment of a plurality of MRI agents to polymers. A "polymer" comprises at least two or three subunits, which are covalently attached. At least some portion of the monomeric subunits contain functional groups for the covalent attachment of the MRI contrast agents. In some embodiments coupling moieties are used to covalently link the subunits with the MRI agents. As will be appreciated by those in the art, a wide variety of polymers are possible. Suitable polymers include functionalized styrenes, such as amino styrene, functionalized dextrans, and polyamino acids. Preferred polymers are polyamino acids (both poly-D-amino acids and poly-L-amino acids), such as polylysine, and polymers containing lysine and other amino acids being particularly preferred. Other suitable polyamino acids are polyglutamic acid, polyaspartic acid, co-polymers of lysine and glutamic or aspartic acid, co-polymers of lysine with alanine, tyrosine, phenylalanine, serine, tryptophan, and/or proline.

Similarly, it is also possible to create "multimers" of MRI agents, by either direct attachment or through the use of linkers as is generally described in U.S. Ser. No. 08/690,612 (allowed), incorporated by reference.

Once synthesized, the metal ion complexes of the invention have use as magnetic resonance imaging contrast or enhancement agents. Specifically, the functional MRI agents of the invention have several important uses, including the non-invasive imaging of drug delivery, imaging the interaction of the drug with its physiological target, monitoring gene therapy, in vivo gene expression (antisense), transfection, changes in intracellular messengers as a result of drug delivery, etc.

The metal ion complexes of the invention may be used in a similar manner to the known gadolinium MRI agents. See for example, Meyer et al., supra; U.S. Pat. No. 5,155,215; U.S. Pat. No. 5,087,440; Margerstadt et al., Magn. Reson. Med. 3:808 (1986); Runge et al., Radiology 166:835 (1988); and Bousquet et al., Radiology 166:693 (1988). The metal ion complexes are administered to a cell, tissue or patient as is known in the art. A "patient" for the purposes of the present invention includes both humans and other animals and organisms, such as experimental animals. Thus the methods are applicable to both human therapy and veterinary applications. In addition, the metal ion complexes of the invention may be used to image tissues or cells; for example, see Aguayo et al., Nature 322:190 (1986).

Generally, sterile aqueous solutions of the contrast agent complexes of the invention are administered to a patient in a variety of ways, including orally, intrathecally and especially intravenously in concentrations of 0.003 to 1.0 molar, with dosages from 0.03, 0.05, 0.1, 0.2, and 0.3 millimoles per kilogram of body weight being preferred. Dosages may depend on the structures to be imaged. Suitable dosage levels for similar complexes are outlined in U.S. Pat. Nos. 4,885,363 and 5,358,704.

In addition, the contrast agents of the invention may be delivered via specialized delivery systems, for example, within liposomes (see Navon, Magn. Reson. Med. 3:876–880 (1986)) or microspheres, which may be selectively taken up by different organs (see U.S. Pat. No. 5,155,215).

In some embodiments, it may be desirable to increase the blood clearance times (or half-life) of the MRI agents of the invention. This has been done, for example, by adding carbohydrate polymers to the chelator (see U.S. Pat. No. 5,155,215). Thus, one embodiment utilizes polysaccharides as substitution R groups on the compositions of the invention.

A preferred embodiment utilizes complexes which cross the blood-brain barrier. Thus, as is known in the art, a DOTA derivative which has one of the carboxylic acids replaced by an alcohol to form a neutral DOTA derivative has been shown to cross the blood-brain barrier. Thus, for example, neutral complexes are designed that cross the blood-brain barrier with therapeutic blocking moieties to treat disorders of the brain.

The references cited herein are expressly incorporated by reference in their entirety.

I claim:

1. A method comprising:
   a) administering an MRI agent having the formula comprising:

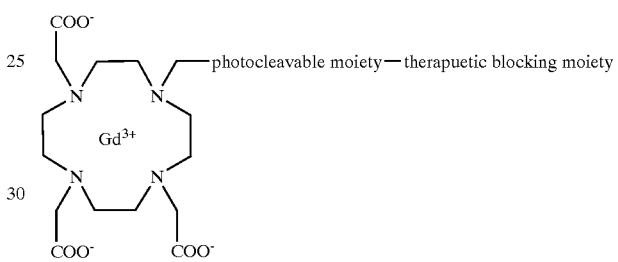

b) exposing said MRI agent to light to cleave said photocleavable moiety such that the exchange of water in at least one coordination site of said MRI agent is increased; and,
   c) producing a magnetic resonance image of a cell, tissue, or patient and eliciting a therapeutic effect.

2. A method comprising:
   a) administering an MRI agent having the formula comprising:

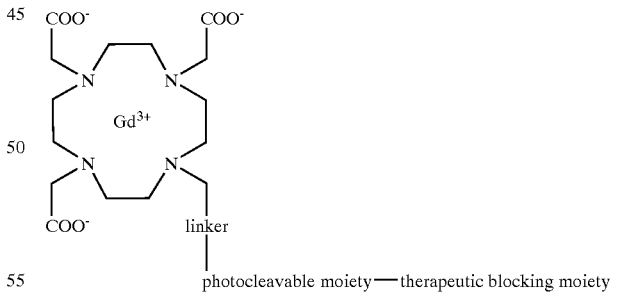

wherein said linker is an aryl or alkyl group;
   b) exposing said MRI agent to light to cleave said photocleavable moiety such that the exchange of water in at least one coordination site of said MRI agent is increased; and,
   c) producing a magnetic resonance image of a cell, tissue, or patient and eliciting a therapeutic effect.

3. A method comprising:
   a) administering an MRI agent having the formula comprising:

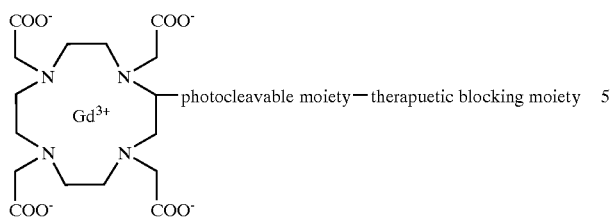

b) exposing said MRI agent to light to cleave said photocleavable moiety such that the exchange of water in at least one coordination site of said MRI agent is increased; and, c) producing a magnetic resonance image of a cell, tissue, or patient and eliciting a therapeutic effect.

4. A method according to claims 1, 2, or 3, wherein said photocleavable moiety comprises O-nitrobenzylic compounds.

5. A method according to claims 1, 2, or 3, wherein said therapeutic blocking moiety comprises cytokines.

6. A method according to claims 1, 2, or 3, wherein said photocleavable moiety comprises benzoin-based moieties.

7. A method according to claims 1, 2, or 3, wherein said therapeutic blocking moiety comprises enzyme inhibitors.

8. A method according to claims 1, 2, or 3, wherein said therapeutic blocking moiety comprises metal ion complexes.

9. A method according to claims 1, 2, or 3, wherein said therapeutic blocking moiety comprises toxins.

10. A method according to claims 1, 2, or 3, wherein said therapeutic blocking moiety comprises antibodies.

11. A method according to claims 1, 2, or 3, wherein said therapeutic blocking moiety comprises transcription factors.

12. A method according to claims 1, 2, or 3, wherein said therapeutic blocking moiety comprises nucleic acids.

13. A method according to claim 2, wherein said alkyl and said aryl group are selected from the group consisting of substituted alkyl, heteroalkyl, substituted heteroalkyl, substituted aryl, heteroaryl and substituted heteroaryl.

14. A method comprising:

a) administering an MRI agent having the formula comprising:

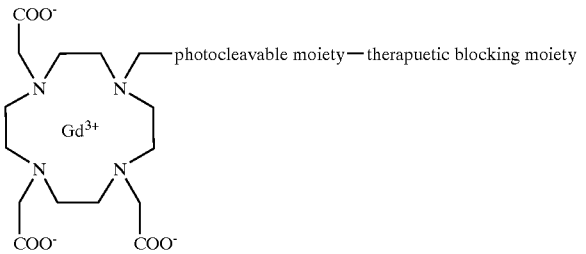

b) exposing said MRI agent to light to cleave said photocleavable moiety, wherein upon cleavage of said photocleavable moiety the $T_1$ of the agent is decreased, and, c) producing a magnetic resonance image of a cell, tissue, or patient and eliciting a therapeutic effect.

15. A method comprising:

a) administering an MRI agent having the formula comprising:

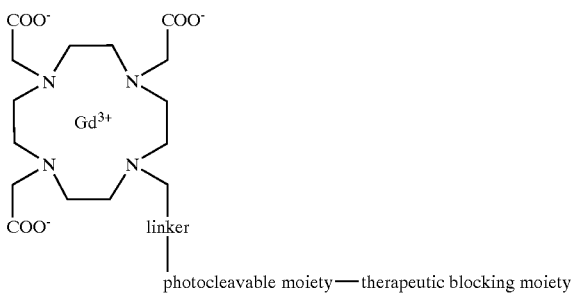

wherein said linker is an aryl or alkyl group selected from the group consisting of substituted alkyl, heteroalkyl, substituted heteroalkyl, substituted aryl, heteroaryl and substituted heteroaryl;

b) exposing said MRI agent to light to cleave said photocleavable moiety wherein upon cleavage of said photocleavable moiety the $T_1$ of the agent is decreased; and, c) producing a magnetic resonance image of a cell, tissue, or patient and eliciting a therapeutic effect.

16. A method comprising:

a) administering an MRI agent having the formula comprising:

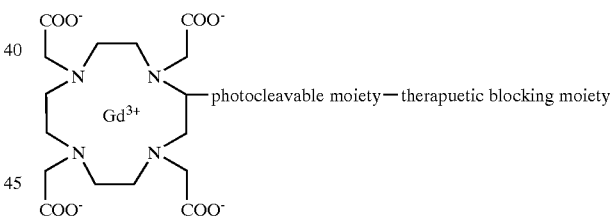

b) exposing said MRI agent to light to cleave said photocleavable moiety wherein upon cleavage of said photocleavable moiety the $T_1$ of the agent is decreased; and, c) producing a magnetic resonance image of a cell, tissue, or patient and eliciting a therapeutic effect.

* * * * *